United States Patent
Liu et al.

(10) Patent No.: US 9,382,202 B2
(45) Date of Patent: Jul. 5, 2016

(54) PRECURSOR FOR LABELING THERAPEUTIC AGENT FOR LIVER CANCER AND METHOD FOR MANUFACTURING THE SAME

(71) Applicant: ATOMIC ENERGY COUNCIL—INSTITUTE OF NUCLEAR ENERGY RESEARCH, Taoyuan County (TW)

(72) Inventors: Show-Wen Liu, Taoyuan County (TW); Yu Chang, Taoyuan County (TW); Cheng-Fang Hsu, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 127 days.

(21) Appl. No.: 14/272,682

(22) Filed: May 8, 2014

(65) Prior Publication Data

US 2015/0322005 A1   Nov. 12, 2015

(51) Int. Cl.
*C07F 13/00*   (2006.01)
*C07C 323/25*   (2006.01)
*C07C 319/20*   (2006.01)
*A61K 51/04*   (2006.01)

(52) U.S. Cl.
CPC ............. *C07C 323/25* (2013.01); *C07C 319/20* (2013.01); *C07F 13/00* (2013.01); *A61K 51/0474* (2013.01)

(58) Field of Classification Search
None
See application file for complete search history.

(56) References Cited

U.S. PATENT DOCUMENTS 7,964,752 B2 *   6/2011   Liu ..................... C07C 323/41
                                                              564/154

* cited by examiner

*Primary Examiner* — Michael G Hartley
*Assistant Examiner* — Melissa Perreira
(74) *Attorney, Agent, or Firm* — Rosenberg, Klein & Lee

(57) ABSTRACT

A precursor for labeling therapeutic agents for liver cancer and a method for manufacturing the same are revealed. The chemical structure of the precursor has a ligand linked to complex compounds of radioisotopes. Moreover, the chemical structure of the precursor further includes a specific functional group soluble in Lipiodol or having properties of Lipiodol. Thus the radioisotopes attached to the precursor are allowed to retain in hepatic tissues of patients with liver cancer for internal radiation therapy of liver cancer.

12 Claims, 8 Drawing Sheets

PRECURSOR FOR LABELING THERAPEUTIC AGENT FOR LIVER CANCER AND METHOD FOR MANUFACTURING THE SAME

FIELD OF THE INVENTION

The present invention relates to a precursor for labeling therapeutic agents and a method for manufacturing the same, especially to compounds L-Nε-[2-(Triphenylmethyl)thioacetyl]-Nα-8-heptadecenylcarbonyl-6-aza-5-oxo-9-(triphenyl methyl)thio-1,5-nonanediamine (hereafter called HOC-NODA) and L-Nε-[2-(Triphenylmethyl)thioacetyl]-Nα-5,6-diiodotetradecylcarbonyl-6-aza-5-oxo-9-(triphenylmethyl) thio-1,5-nonanediamine (hereafter called TDI-NODA) that are linked to radioisotopes for treatment of liver cancers.

BACKGROUND OF THE INVENTION

Primary carcinoma of the liver is one of common malignant tumors. About 260,000 new cases are diagnosed each year, which is approximately 4% of all cancer types. In recent years, the incident rate is increasing and this affects our health significantly. Thus, seeking advanced techniques for diagnosis and treatment of liver cancer have become more important.

There are various types of treatment for liver cancer. The main treatments include surgery, embolization, injecting alcohol into the tumor, injecting acetic acid into the tumor, microwave ablation, cryotherapy, chemotherapy, radiotherapy, immunotherapy, and supportive therapy. According to hepatocellular carcinoma therapeutic guideline of American Association for the Study of Liver Diseases, early treatment of patients is effective. Patients can be cured by surgery and tumor ablation. The 5-year survival rate is 50%-75%. Patients in the intermediate stage can only accept embolization, and the 3-year survival rate is 50%. At late stage, the 1-year survival rate drops to 50% or even lower.

What makes liver cancer so deadly? The liver tumors are growing quickly and typically diagnosed in the intermediate stage or late stage. In late stage cases, there is a significantly decreased treatment effect. Yet once late-stage patients are treated by a target therapy, their survival time is increased, the risk of death is reduced and the life quality is improved.

Lipiodol is an iodinated ester derived from poppy seed oil, and it is concentrated and selectively retained in hepatic tumor cells. Transcatheter infusion of Lipiodol via the hepatic artery has been used increasingly for diagnosis and treatment of hepatic cancers. Even tiny malignant tumors have been detected. Thus Lipiodol has a great potential as a carrier for chemotherapeutic or radiotherapeutic agents for targeted therapy.

Recently targeted therapy drugs have been broadly applied to cancer treatment. Targeted therapy blocks the growth of cancer cells by interfering with specific targeted molecules involved in carcinogenesis, tumor growth or repair processes such as cell transformation, proliferation or metastasis. The drugs can also inhibit tumor angiogenesis or block tumor nutrient supply so as to inhibit growth, accelerate apoptosis and prevent cancer spreading. The specific targeted molecules include tumor enzymes, small molecules in tumor cells, and antigens on tumor cell surfaces. Compared with conventional chemotherapy, targeted therapy is highly-selective and with much fewer side effects.

Rhenium-188 ($^{188}$Re) is a radionuclide that emits beta and gamma rays, and having a half life of 16.9 hours. It is produced in a nuclear reactor and is convenient to use. The radiant energy and the half life of $^{188}$Re are optimal for disease diagnosis and treatment so that $^{188}$Re is a medical radioisotope with great potential in internal radiation therapy. Therefore $^{188}$Re-labeled Lipiodol ([188Re]-Lipiodol) is considered as a potential radiopharmaceutical agent for treatment of liver tumors.

If a precursor for labeling therapeutic agents is highly soluble in Lipiodol and is having selective retention property of Lipiodol in hepatic carcinoma tissues, it provides great help in treatment of liver cancer.

SUMMARY

Therefore it is a primary object of the present invention to provide a precursor for labeling therapeutic agents for liver cancer whose chemical structure has a ligand and a specific functional group. The ligand connects/links to complex compounds of radioisotopes while specific functional group enables the precursor for labeling therapeutic agents for liver cancer soluble in Lipiodol or having properties of Lipiodol. Thus the radioisotope can be retained in patients' hepatic tumor cells for internal radiation therapy.

It is another object of the present invention to provide a method for manufacturing precursor for labeling therapeutic agents for liver cancer in which a ligand structure and specific functional groups are formed in turn by a series of chemical reactions so as to produce compound HOC-NODA or TDI-NODA. Both HOC-NODA and TDI-NODA are useful in treatment of liver cancer and able to be applied to novel therapeutic agents for treatment of liver tumors.

In order to achieve above objects, a precursor for labeling therapeutic agents for liver cancer and a method for manufacturing the same according to the present invention are provided. The structural formula of the precursor is as following:

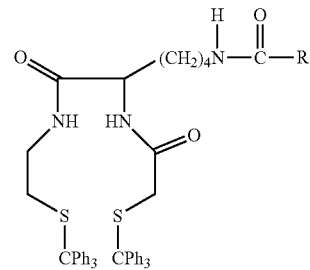

wherein a functional group R is 8-heptadecenyl group or 5,6-diiodotetradecyl group.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION

Please refer to following embodiments for details, features and effects of the present invention.

Figure 1:
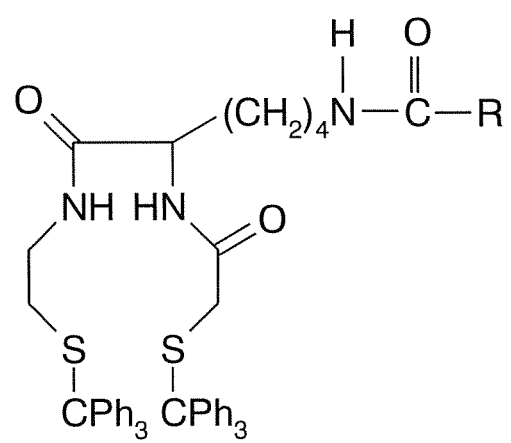
FIG. 1 shows a chemical structure of an embodiment of a precursor for labeling therapeutic agents for liver cancer according to the present invention.
Figure 2:
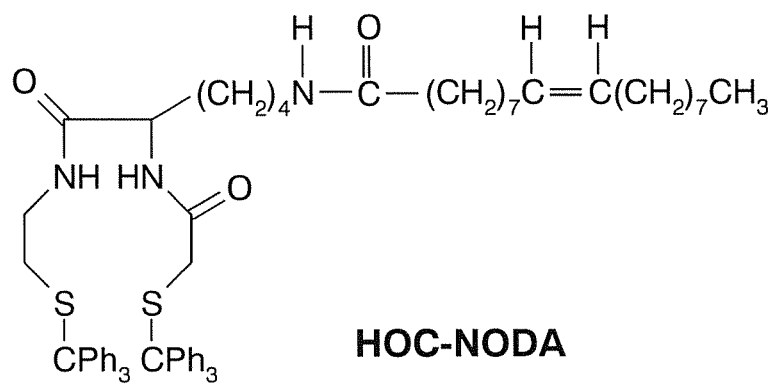
FIG. 2 shows a chemical structure of HOC-NODA, a precursor for labeling therapeutic agents for liver cancer, of the present invention.
Figure 3:
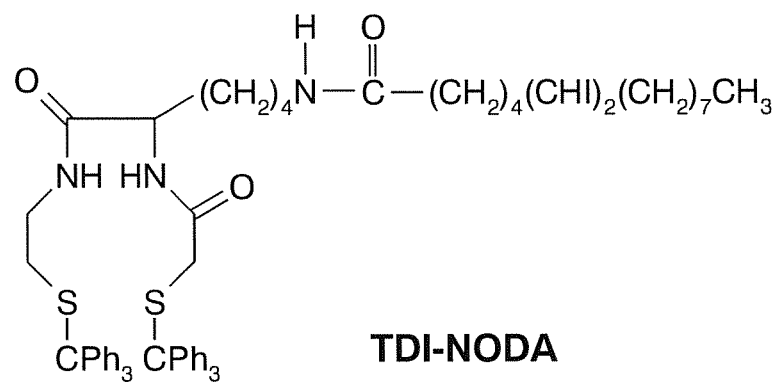
FIG. 3 shows a chemical structure of TDI-NODA, a precursor for labeling therapeutic agents for liver cancer, of the present invention.

Refer to FIG. 1, a chemical structure of a precursor for labeling therapeutic agents for liver cancer of the present invention is revealed. R includes two different functional groups. As shown in FIG. 2, the precursor is HOC-NODA when R is 8-heptadecenyl group. If R is 5,6-diiodotetradecyl group, as shown in FIG. 3, the precursor is TDI-NODA. Products with different functional groups are obtained by different reactants. On one hand, the structure of HOC-NODA includes a long-chain alkyl group that raises lipid solubility so that its complex compounds are easy to be dissolved in Lipiodol and retained in hepatic carcinoma tissues longer. On the other hand, HOC-NODA is able to bond with $ReO^{3+}$ and used to prepare Re-labeled radiopharmaceuticals. As to TDI-NODA with Lipiodol structure, it can be retained in hepatic carcinoma tissues and bonded to $ReO^{3+}$ directly without being dissolved in Lipiodol in advance. Both HOC-NODA and TDI-NODA are useful in disease treatment. After linked to radioisotopes such as $^{188}Re$ or $^{99m}Tc$, labeling substances for therapeutic agents for liver cancer are obtained and are applied to radiopharmaceutical agents for liver tumors.

A method for manufacturing for precursors for labeling therapeutic agents for liver cancer includes following steps shown from FIG. 4 to FIG. 9.

Figure 4:
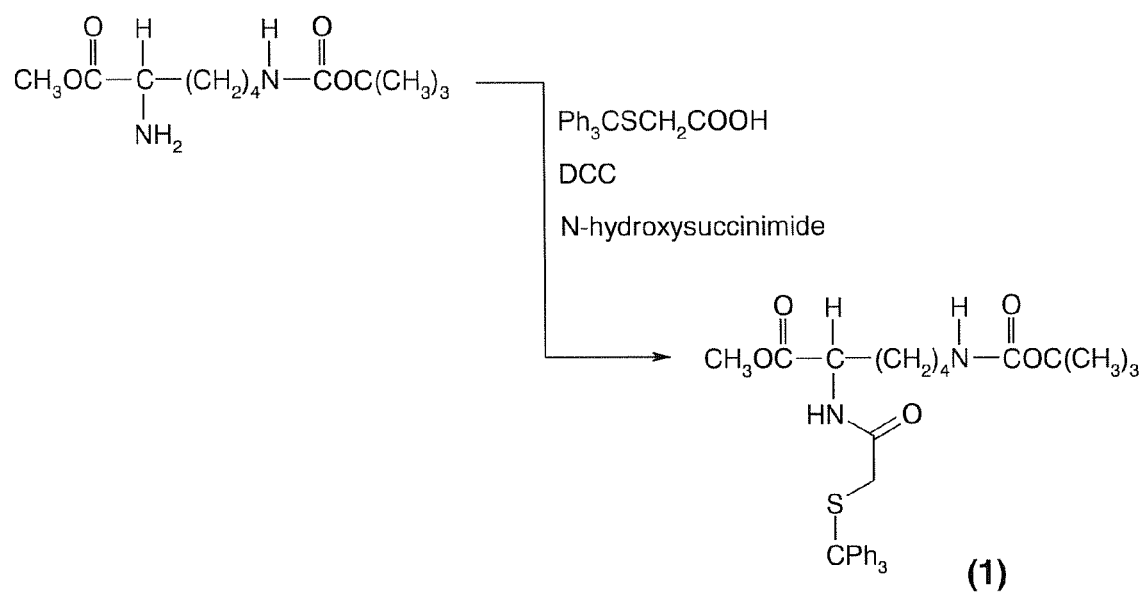
FIG. 4 is a schematic diagram showing a part of chemical reactions involved in synthesis of a precursor for labeling therapeutic agents for liver cancer according to the present invention.

Step S1: refer to FIG. 4, produce L-Nε-tert-butoxycarbonyl-Nα-[2-(triphenylmethyl)thioacetyl]lysine methyl ester (hereafter called compound 1) by an amidation reaction between L-Nε-tert-butoxycarbonyllysine methyl ester and triphenylmethyl thio glycolic acid.

Figure 5:
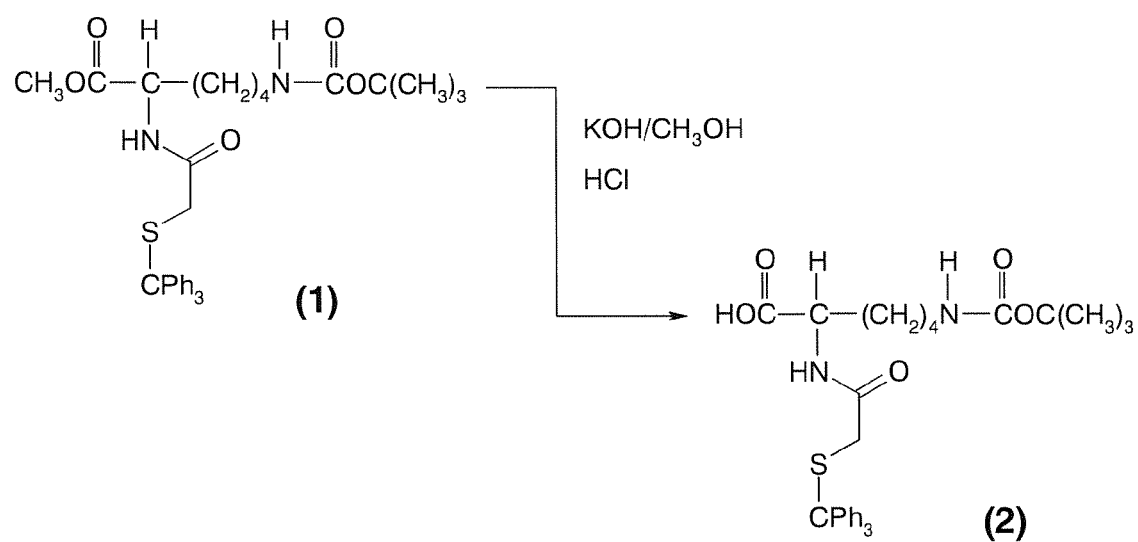
FIG. 5 is a schematic diagram showing a part of chemical reactions involved in synthesis of a precursor for labeling therapeutic agents for liver cancer according to the present invention.

Step S2: refer to FIG. 5, hydrolyze the compound 1 to produce L-Nε-tert-butoxycarbonyl-Nα-[2-(triphenylmethyl)thioacetyl]lysine (hereafter called compound 2).

Figure 6:
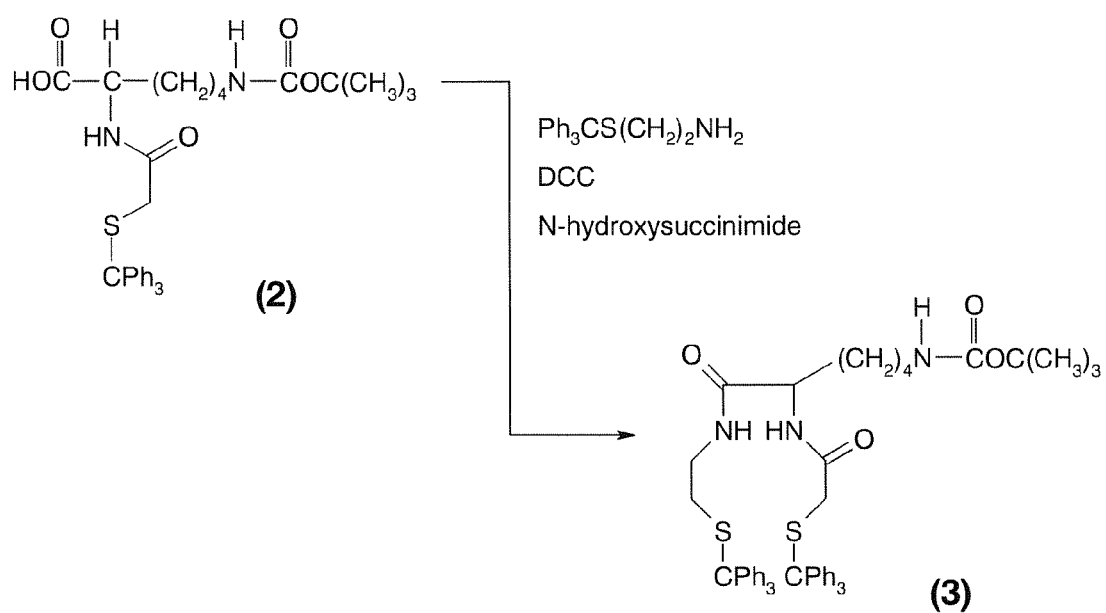
FIG. 6 is a schematic diagram showing a part of chemical reactions involved in synthesis of a precursor for labeling therapeutic agents for liver cancer according to the present invention.

Step S3: refer to FIG. 6, produce L-Nε-tert-butoxycarbonyl-Nα-[2-(triphenylmethyl)thioacetyl]-6-aza-5-oxo-9-(triphenyl methyl)thio-1,5-nonanediamine (hereafter called compound 3) by an amidation reaction between the compound 2 and 2-(triphenylmethyl)thio]ethylamine.

Figure 7:
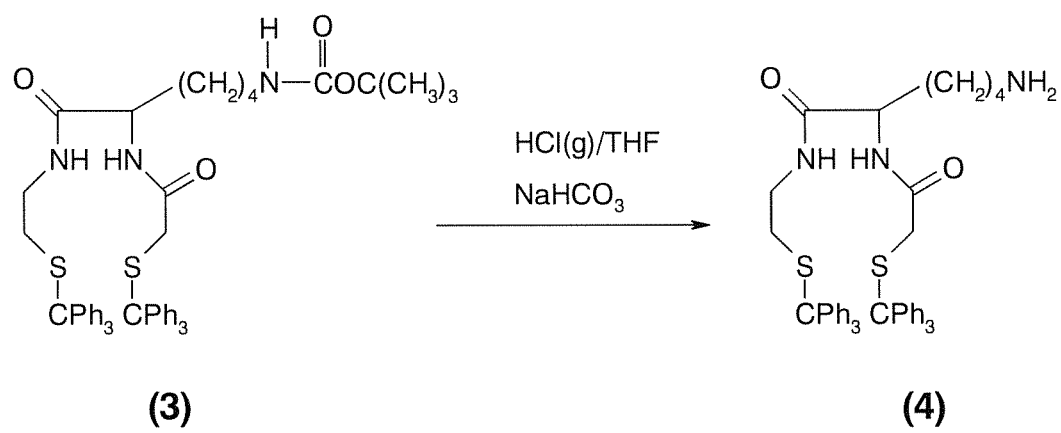
FIG. 7 is a schematic diagram showing a part of chemical reactions involved in synthesis of a precursor for labeling therapeutic agents for liver cancer according to the present invention.
Figure 8:
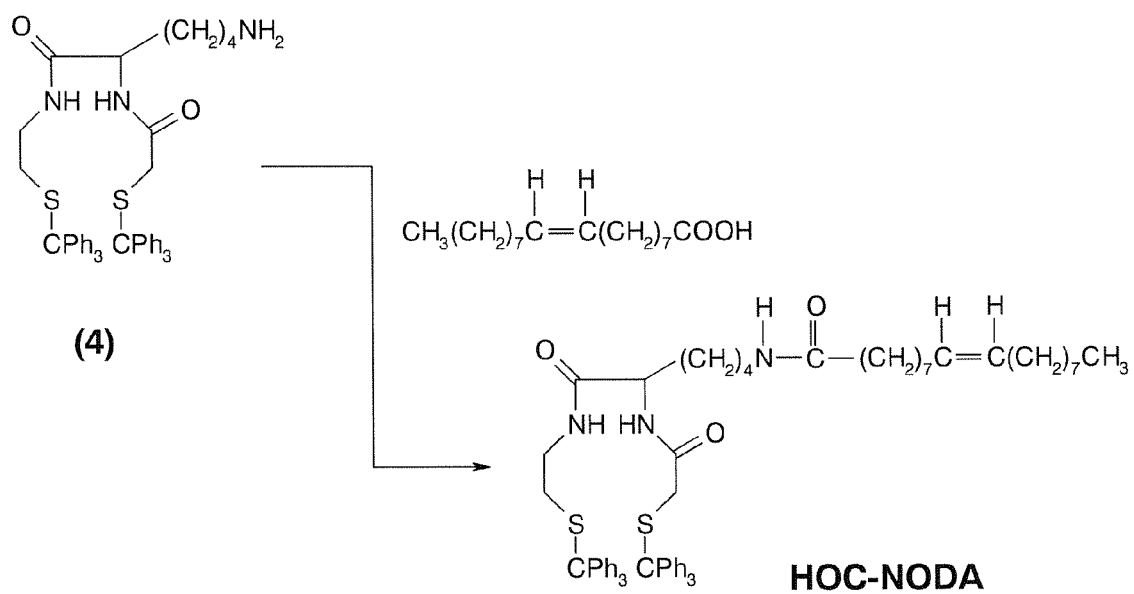
FIG. 8 is a schematic diagram showing a part of chemical reactions involved in synthesis of a precursor for labeling therapeutic agents for liver cancer according to the present invention.
Figure 9:
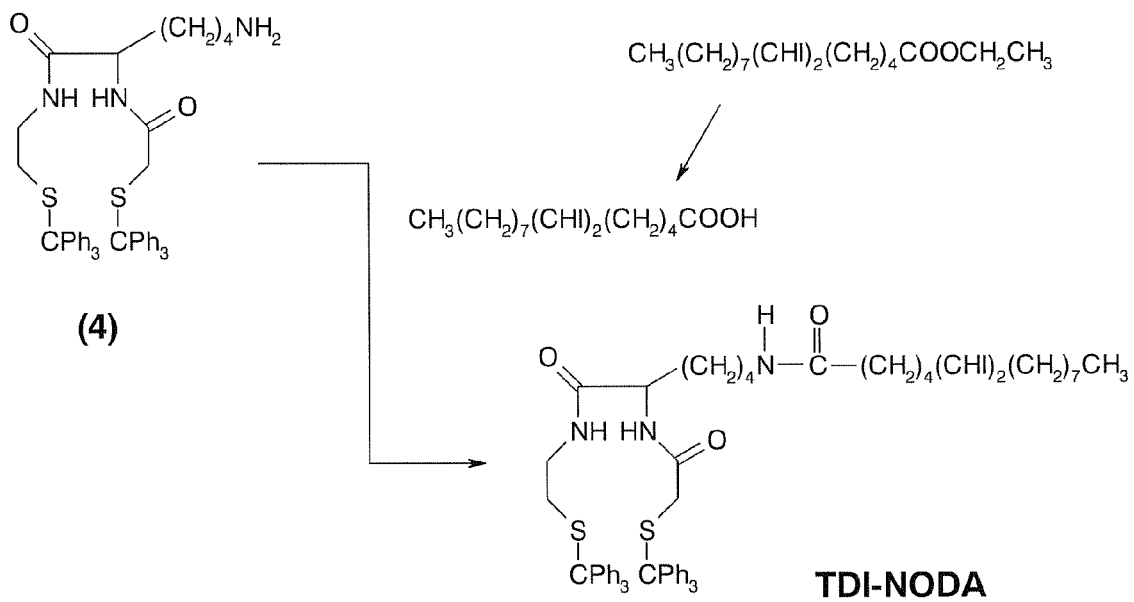
FIG. 9 is a schematic diagram showing a part of chemical reactions involved in synthesis of a precursor for labeling therapeutic agents for liver cancer according to the present invention.

Step S4: refer to FIG. 7, decompose the compound 3 by acid to produce L-Nε-[2-(triphenylmethyl)thioacetyl]-6-aza-5-oxo-9-(triphenylmethyl)thio-1,5-nonanediamine (hereafter called compound 4);

Step S5: refer to FIG. 8 and FIG. 9, carry out an amidation reaction between the compound 4 and oleic acid/or 6,7-diiodotetradecanoic acid to produce HOC-NODA/or TDI-NODA.

HOC-NODA and TDI-NODA produced by the present invention have specific structure for protecting thiol groups thereof. Thiols are easily be oxidized in neutral or alkaline solution. The oxidized thiol group is unable to react with radioisotopes. Thus the thiols need to be protected in advance. There are various ways to protect the thiol group and triphenylmethyl is used to protect two thiol groups in HOC-NODA and TDI-NODA in the present invention. Thus both HOC-NODA and TDI-NODA have stable chemical properties which result in convenience in room temperature storage. The bond energy between triphenylmethyl group and sulfur atom is lower. When heavy metals are present, the bond therebetween is easy to break and a bond between heavy metals and sulfur atom is formed. Thus the triphenylmethyl group for protection is automatically released during complex reaction between thiol group and technetium-99m ($^{99m}Tc$) or Rhenium-188 ($^{188}Re$). There is no need to remove the protection group in advance.

While in use, HOC-NODA/TDI-NODA is dissolved in trifluoroacetic acid and overdose triethylsilane is added into the solution. Thus triphenylmethyl group is released from thiol group to form solid that is insoluble in trifluoroacetic acid. Then the solid can be removed by filtration or wash with n-hexane. These methods are simple and convenient.

The followings are data controlled during synthesis of HOC-NODA/TDI-NODA and analysis results of the synthesis products.

Synthesis of compound 1: 15.4 g (51.7 mmol) L-Nε-tert-butoxycarbonyllysine methyl ester hydrochloride, 17.3 g (51.7 mmol) triphenylmethyl thioglycolic acid, 21.5 mL (155.1 mmol) triethylamine, together with 16 (77.6 mmol) 1,3-dicyclohexylcarbodiimide and 7.14 g (62.0 mmol) N-hydroxysuccinimide used as reactive agents are dissolved in 250 mL chloroform and heat the solution at 50° C. overnight. Reaction time is 24 hours. Remove solid by vacuum filtration and dry the filtrate by vacuum evaporation. Dissolve residue by 150 mL acetone. Then dry the filtrate by vacuum evaporation after filtration. Use liquid chromatography ($SiO_2$, $CHCl_3$:EtOAc=4:1) for isolation and purification to get solid product-compound 1 (23.5 g, 79%).

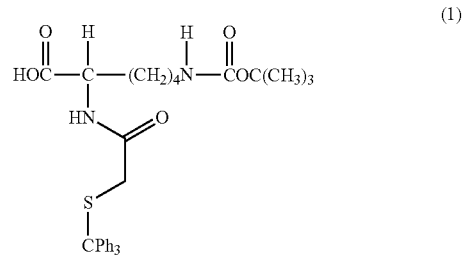

Analysis of the Synthesis Product-Compound 1:

IR (KBr) 3337 (NH), 1742 and 1669 (CO) cm$^{-1}$. $^1$H NMR ($CDCl_3$) 7.39-7.17 (m, 15H, Ph), 6.51 (d, J=7.5 Hz, 1H, NHCH), 4.51 (br, 1H, NHCH$_2$), 4.30 (q, J=6.0 Hz, 1H, NCH), 3.69 (s, 3H, OCH$_3$), 3.06 (s, 2H, CH$_2$S), 3.02 (m, 2H, CH$_2$N), 1.65 (m, 2H, CHCH$_2$), 1.50 (m, 2H, CH$_2$CH$_2$NH), 1.40 (s, 9H, C(CH$_3$)$_3$), 1.68 (m, 2H, CH$_2$CH$_2$CH). $^{13}$C NMR (CDCl$_3$) 172.23, 167.88 and 155.90 (CO), 143.95, 192.51, 128.09 and 127.0 (Ph), 77.18 (C(CH$_3$)$_3$), 67.93 (CPh$_3$), 52.27 and 52.15 (CH$_3$O and CH), 40.15 (CH$_2$NH), 36.06, 32.01, 29.47 and 22.29 (CH$_2$), 28.37 (C(CH$_3$)$_3$).

Synthesis of compound 2: Dissolve 23.54 g (40.8 mmol) compound 1 in 400 mL methanol solution containing 10% potassium hydroxide. Used as a catalyst, potassium hydroxide can be replaced by sodium methoxide. Then stir the solution at room temperature for 30 min and cool down the solution in an ice bath. Add 140 mL water for hydrolysis and drop concentrated hydrochloric acid into the solution for adjusting the pH value of the solution to 6.0. Extract by dichloromethane (3×80 mL). The organic phase is dehydrated by anhydrous sodium sulfate and dried by vacuum evaporation to get solid product-compound 2 (23 g, 100%).

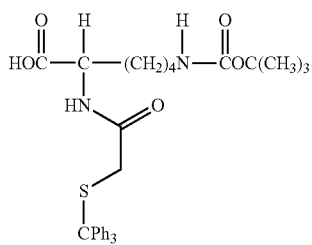

(2)

Analysis of the Synthesis Product-Compound 2:
IR (KBr) 3348 (NH), 1714 and 1659 (CO) cm$^{-1}$. $^1$H NMR (DMSO-d$_6$) 8.24 (d, J=7.8 Hz, 1H, NHCH), 7.43-7.28 (m, 15H, Ph), 6.80 (br, 1H, NHCH$_2$), 4.12 (m, 1H, CH), 2.92 (m, 4H, CH$_2$S and CH$_2$NH), 1.69-1.20 (m, 6H, CH$_2$CH$_2$CH$_2$CH), 1.41 (s, 9H, C(CH$_3$)$_3$). $^{13}$C NMR (DMSO-d$_6$) 173.28, 167.37 and 155.52 (CO), 144.08, 129.06, 128.05 and 126.76, (Ph), 77.29 (C(CH$_3$)$_3$), 65.91 (CPh$_3$), 52.10 (CH), 39.23, 35.74, 30.58, 29.05 and 22.68 (CH$_2$), 28.23 (CH$_3$).

Synthesis of compound 3: 21.7 g (38.6 mmol) Compound 2, 12.3 g (38.6 mmol) 2-(triphenylmethyl)thio]ethylamine, 16 mL (115.8 mmol) triethylamine, together with 12 g (57.9 mmol 1,3-dicyclohexylcarbodiimide and 5.33 g (46.3 mmol) N-hydroxysuccinimide used as reactive agents are dissolved in 250 mL chloroform and heat the solution at 50° C. overnight. The solution is treated by vacuum filtration and the filtrate is taken. Wash organic phase with 100 mL saturated aqueous solution of sodium bicarbonate and remove the solvent by vacuum evaporation. Dissolve residue with 100 mL acetone and remove insoluble substances after vacuum filtration. Then the filtrate is concentrated by vacuum evaporation. Use liquid chromatography (SiO$_2$, CHCl$_3$:CH$_3$OH=95:5) for isolation and purification to get product-compound 3 (25.7 g, 77%).

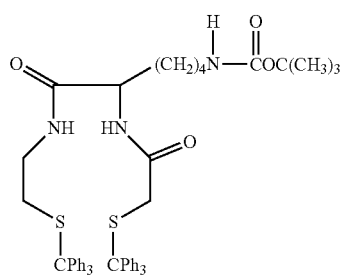

(3)

Analysis of the Synthesis Product-Compound 3:
IR (neat) 3290 (NH), 1688 and 1642 (CO) cm$^{-1}$. $^1$H NMR (CDCl$_3$) 7.40-7.16 (m, 30H, Ph), 6.36 (d, J=7.8 Hz, 1H, NHCH), 6.05 (br, 1H, NH(CH$_2$)$_2$S), 4.55 (br, 1H, NH(CH$_2$)$_4$), 4.02 (q, J=7.2 Hz, 1H, CHNH), 3.03 (m, 6H, CH$_2$CH$_2$S, COCH$_2$S and NHCH$_2$(CH$_2$)$_3$), 2.36 (t, J=6.6 Hz, 2H, CH$_2$CH$_2$S), 1.78-1.13 (m, 6H, (CH$_2$)$_3$CH), 1.42 (s, 9H, C(CH$_3$)$_3$). $^{13}$C NMR (CDCl$_3$) 170.53, 168.20 and 155.87 (CO), 144.49, 143.87, 129.41, 128.06, 127.87, 126.96 and 126.69 (Ph), 77.13 (C(CH$_3$)$_3$), 67.86 and 66.72 (CPh$_3$), 52.98 (CH), 40.06, 38.17, 36.0, 31.68, 31.55, 29.47 and 22.50 (CH$_2$), 28.33 (C(CH$_3$)$_3$).

Synthesis of compound 4: Dissolve 25.7 g (29.7 mmol) compound 3 in 800 mL anhydrous tetrahydrofuran (THF) solution and introduce hydrogen chloride gas used as a reactive agent for acid decomposition. Once the solution is saturated, stir the solution at room temperature for 1 hour. Isolate the solid by suction filtration. Wash the solid with 100 mL ether and get insoluble material. Dissolve the insoluble in dichloromethane and wash organic phase with 100 mL saturated sodium bicarbonate solution. The organic phase is dried by Anhydrous sodium sulfate and concentrated by vacuum evaporation. Use liquid chromatography (SiO$_2$, CHCl$_3$:CH$_3$OH=70:30) for isolation and purification to get product-compound 4 (16.5 g, 73%).

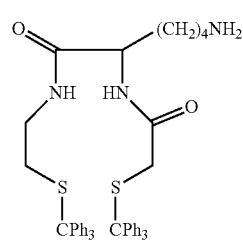

(4)

Analysis of the Synthesis Product-Compound 4:
IR (neat) 3287 (NH), 1644 (CO) cm$^{-1}$. $^1$H NMR (CDCl$_3$) 7.41-7.17 (m, 30H, Ph), 6.52 (d, J=7.8 Hz, NHCH), 6.45 (t, J=5.4 Hz, 1H, NHCH$_2$), 4.07 (q, J=7.5 Hz, 1H, CHNH), 3.01 (m, 4H, CH$_2$CH$_2$S and CH$_2$S), 2.63 (t, J=6.6 Hz, 2H, CH$_2$NH$_2$), 2.37 (m, 2H, CH$_2$CH$_2$S), 1.92 (br, 2H, NH$_2$), 1.67-1.18 (m, 6H, (CH$_2$)$_3$CH). $^{13}$C NMR (CDCl$_3$) 170.71 and 168.20 (CO), 144.57, 143.94, 129.47, 128.09, 127.92, 126.99 and 126.74 (Ph), 67.85 and 66.74 (CPh$_3$), 53.07 (CH), 41.44, 38.23, 36.13, 32.46, 32.01, 31.65 and 22.49 (CH$_2$).

Synthesis of 6,7-diiodotetradecanoic acid: Dissolve 12.8 g (23.9 mmol) Lipiodol in 400 mL methanol solution containing 10% potassium hydroxide. Used as a catalyst, potassium hydroxide can be replaced by sodium methoxide. The solution is stirred at room temperature for 3 hours and concentrated. Then add 20 mL methanol and 20 mL water for hydrolysis. Set the solution in an ice bath and add concentrated hydrochloric acid into the solution for adjusting the pH value of the solution to 6.0. Extract by dichloromethane (3×100 mL). The organic phase is dehydrated by anhydrous sodium sulfate and dried by vacuum evaporation to get a product-6,7-diiodotetradecanoic acid (12.1 g, 100%).

Analysis of the Synthesis Product-6,7-diiodotetradecanoic Acid:
IR (neat) 2950 (OH), 1620 (CO) cm$^{-1}$. $^1$H NMR (CD$_3$OD) 4.17-4.15 (m, H, (CHI)$_2$), 2.20 (t, 2H, C$\underline{H}_2$COOH), 2.06-1.28 (m, 10H, CH$_2$), 0.94-0.90 (m, 3H, CH$_3$). $^{13}$C NMR (CD$_3$OD) 179.32 (CO), 40.36 and 40.29, (CHI)$_2$), 35.99 (C$\underline{H}_2$COOH), 29.41, 29.38, 29.31, 29.22, 29.19, 29.12, 28.89, 25.65, 22.27 (CH$_2$), 13.07 (CH$_3$).

synthesis of HOC-NODA: 1.14 g (1.49 mmol) Compound 4, 0.48 mL (1.49 mmol) oleic acid, 0.62 mL (4.47 mmol) triethylamine, together with 0.46 g (2.24 mmol) 1,3-dicyclohexylcarbodiimide and 0.20 g (1.79 mmol) N-hydroxysuccinimide used as reactive agents are dissolved in 100 mL chloroform and heat the solution at 50° C. overnight. Reaction time is 24 hours. Concentrate the solution by vacuum evaporation. Dissolve residue by 100 mL acetone and remove insoluble substances after vacuum, filtration. Then the filtrate is concentrated by vacuum evaporation. Use liquid chromatography ($SiO_2$, $CHCl_3$:$CH_3OH$=95:5) for isolation and purification to get the product-HOC-NODA (1.15 g, 75%).

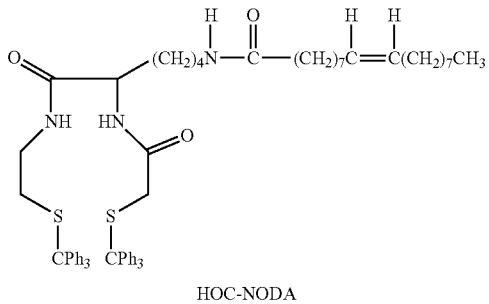

HOC-NODA

Analysis of the Synthesis Product-HOC-NODA:

IR (neat) 3285 (NH), 1640 (CO) $cm^{-1}$. $^1H$ NMR ($CDCl_3$) 7.40-7.16 (m, 30H, Ph), 6.48 (d, NHCH), 6.27 (t, 1H, $NHCH_2$), 5.73 (q, 1H, CHNH), 5.33 (q, 2H, $COCH_2$), 4.08 (q, 1H, CHNH), 3.15 (q, 2H, $CH_2NH$), 3.02 (m, 4H, $CH_2CH_2S$ and $CH_2S$), 2.36 (m, 2H, $CH_2CH_2S$), 2.11-1.88 (m, 8H, $COCH_2CH_2CH_2CH_2CH_2CH_2CH_2$), 1.70-1.55 (m, 6H, $CHCH_2CH_2CH_2CH_2$ and $CH_2CH_2CH=CH$), 1.44 (m, 2H, $CHCH_2CH_2CH_2CH_2$), 1.27-1.06 (m, 16H, $CH_2$), 0.88 (m, 3H, $CH_3$). $^{13}C$ NMR ($CDCl_3$) 173.31, 170.76 and 168.44 (CO), 144.60, 143.97, 129.21, 128.15, 127.97, 127.06 and 126.79 (Ph), 67.91 and 66.79 ($CPh_3$), 52.91 (CH), 38.86, 38.33, 36.78, 36.17, 33.96, 31.90, 31.77, 31.67, 29.77, 29.75, 29.52, 29.32, 29.19, 28.90, 27.23, 27.20, 25.81, 25.65, 24.96, 22.68 and 22.52 ($CH_2$), 14.13 ($CH_3$).

synthesis of TDI-NODA: 1.08 g (1.41 mmol) Compound 4, 0.72 g (1.41 mmol) 6,7-diiodotetradecanoic acid, 0.59 mL (4.24 mmol) triethylamine, together with 0.44 g (2.12 mmol) 1,3-dicyclohexylcarbodiimide and 0.20 g (1.70 mmol) N-hydroxysuccinimide used as reactive agents are dissolved in 100 mL chloroform and heat the solution at 50° C. overnight. Reaction time is 24 hours. Concentrate the solution by vacuum evaporation. Dissolve residue by 100 mL acetone and remove insoluble substances after vacuum filtration. Then the filtrate is concentrated by vacuum evaporation. Use liquid chromatography ($SiO_2$, $CHCl_3$:$CH_3OH$=95:5) for isolation and purification to get the product-TDI-NODA (1.39 g, 79%).

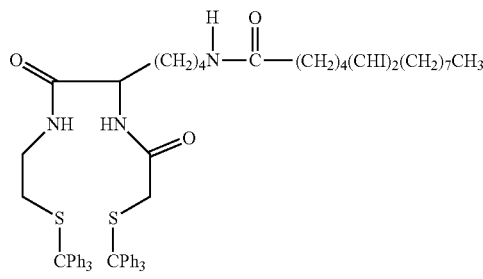

TDI-NODA

Analysis of the Synthesis Product-TDI-NODA:

IR (neat) 3280 (NH), 1650 (CO) $cm^{-1}$. $^1H$ NMR ($CDCl_3$) 7.40-7.19 (m, 30H, Ph), 6.47 (d, NHCH), 6.24 (t, 1H, N $HCH_2$), 5.71 (q, 1H, CHNH), 4.07 (q, 1H, CHNH), 3.17 (q, 2H, $CH_2NH$), 3.02-2.80 (m, 4H, $CH_2CH_2S$ and $CH_2S$), 2.60-2.52 (m, 2H, $(CHI)_2$), 2.38-2.34 (m, 2H, $CH_2CH_2S$), 2.11-2.06 (m, 4H, $COCH_2CH_2CH_2CH_2$), 1.95-1.63 (m, 8H, CHC $H_2CH_2CH_2CH_2CH_2$ and $COCH_2CH_2CH_2CH_2$), 1.59-1.37 (m, 6H, $CHCH_2CH_2CH_2CH_2CH_2CH_2$), 1.28-1.09 (m, 14H, $CH_2$), 0.89-0.86 (m, 3H, $CH_3$). $^{13}C$ NMR ($CDCl3$) 173.26, 170.74 and 168.43 (CO), 144.59, 143.96, 129.51, 128.16, 127.98, 127.07 and 126.80 (Ph), 67.92 and 66.79 ($CPh_3$), 52.90 (CH), 49.03, 40.83, 39.89, 39.70, 38.63, 36.76, 36.15, 31.91, 31.66, 30.97, 30.93, 29.65, 29.28, 28.87, 28.47, 25.77, 25.64, 24.96, 22.59 and 22.51 ($CH_2$), 14.13 ($CH_3$).

In summary, a precursor for labeling therapeutic agents for liver cancer and a method for manufacturing the same are provided by the present invention. HOC-NODA containing long-chain alkyl group and $N_2S_2$ ligand, and TDI-NODA having Lipiodol structure and $N_2S_2$ ligand are used for labeling radioisotopes such as Rhenium-188 ($^{188}Re$) or technetium-99m and applied to radiopharmaceutical agent for treatment of liver tumors. Both compounds have good performance in storage stability, attachment to radioisotopes, and retention in hepatic tissues of patients with liver tumors. Therefore they can be applied to novel therapeutic agents for liver cancer.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

The invention claimed is:

1. A method for manufacturing a precursor for labeling therapeutic agents of liver cancer comprising the steps of:
producing L-Nε-tert-butoxycarbonyl-Nα-[2-(triphenylmethyl)thioacetyl]lysine methyl ester (hereafter called compound 1) by an amidation reaction between L-Nε-tert-butoxycarbonyllysine methyl ester and triphenylmethyl thio glycolic acid;
hydrolyzing the compound 1 to produce L-Nε-tert-butoxycarbonyl-Nα-[2-(triphenylmethyl)thioacetyl]lysine (hereafter called compound 2);
producing L-Nε-tert-butoxycarbonyl-Nα-[2-(triphenylmethyl)thioacetyl]-6-aza-5-oxo-9-(triphenyl methyl) thio-1,5-nonanediamine (hereafter called compound 3) by an amidation reaction between the compound 2 and 2-(triphenylmethyl)thio]ethylamine;
decomposing the compound 3 by acid to produce L-Nε-[2-(triphenylmethyl)thioacetyl]-6-aza-5-oxo-9-(triphenylmethyl)thio-1,5-nonanediamine (hereafter called compound 4); and
carrying out an amidation reaction between the compound 4 and oleic acid/or 6,7-diiodotetradecanoic acid to produce
L-Nε-[2-(Triphenylmethyl)thioacetyl]-Nα-8-heptadecenylcarbonyl-6-aza-5-oxo-9-(triphenyl methyl) thio-1,5-nonanediamine (hereafter called HOC-NODA)/or
L-Nε-[2-(Triphenylmethyl)thioacetyl]-Nα-5,6-diiodotetradecylcarbonyl-6-aza-5-oxo-9-(triphenylmethyl) thio-1,5-nonanediamine (hereafter called TDI-NODA).

2. The method as claimed in claim 1, wherein the HOC-NODA and the TDI-NODA are linked to a radioisotope to form a labeling substance for therapeutic agents for liver cancer; the radioisotope is Rhenium-188 ($^{188}$Re) or technetium-99m ($^{99m}$Tc).

3. The method as claimed in claim 2, wherein the HOC-NODA is dissolved in Lipiodol first and then is linked to the radioisotope to form a labeling substance for therapeutic agents for liver cancer.

4. The method as claimed in claim 2, wherein the TDI-NODA is directly linked to the radioisotope to form a labeling substance for therapeutic agents for liver cancer.

5. The method as claimed in claim 2, wherein the labeling substance for therapeutic agents for liver cancer is applied to a radiopharmaceutical agent for treatment of liver tumors.

6. The method as claimed in claim 1, wherein in the step of decomposing the compound 3 by acid, the step of decomposing the compound 3 by acid is carried out in tetrahydrofuran solution containing hydrogen chloride.

7. The method as claimed in claim 1, wherein the amidation reaction is carried out in chloroform by using 1,3-dicyclohexylcarbodiimide and N-hydroxysuccinimide as reactive agents; reaction temperature is 50° C. and reaction time is 24 hours.

8. The method as claimed in claim 1, wherein in the step of hydrolyzing the compound 1, the hydrolyzing is carried out in methanol solution while a catalyst is potassium hydroxide or sodium methoxide; reaction temperature is room temperature and reaction time is 30 minutes.

9. The method as claimed in claim 1, wherein in the step of decomposing the compound 3 by acid, hydrogen chloride gas is used as a reactive agent and the decomposing is carried out in anhydrous tetrahydrofuran solution; reaction temperature is room temperature and reaction time is 1 hour.

10. The method as claimed in claim 1, wherein in the step of decomposing the compound 3 by acid, reaction temperature is room temperature and reaction time is 1 hour.

11. The method as claimed in claim 1, wherein 6,7-diiodotetradecanoic acid is obtained by hydrolysis of Lipiodol.

12. The method as claimed in claim 11, wherein the hydrolysis of Lipiodol is carried out in methanol solution and a catalyst used is potassium hydroxide or sodium methoxide; reaction temperature is room temperature and reaction time is 3 hours.

* * * * *